United States Patent [19]

Fleet et al.

[11] Patent Number: 5,101,027

[45] Date of Patent: Mar. 31, 1992

[54] SYNTHESIS OF MANNOJIRIMYCIN DERIVATIVES

[75] Inventors: George W. J. Fleet; Ian Bruce, both of Oxford, United Kingdom

[73] Assignee: Monsanto Company, St. Louis, Mo.

[21] Appl. No.: 628,523

[22] Filed: Dec. 17, 1990

Related U.S. Application Data

[60] Division of Ser. No. 419,806, Oct. 11, 1989, Pat. No. 5,011,929, which is a continuation-in-part of Ser. No. 352,068, May 15, 1989, abandoned.

[51] Int. Cl.$^5$ .................................................. C07F 7/02
[52] U.S. Cl. .................................................. 544/69
[58] Field of Search .......................................... 544/69

[56] References Cited

U.S. PATENT DOCUMENTS 4,357,360 11/1982 Light et al. ..................... 426/538

OTHER PUBLICATIONS

Liu, J. Organic Chem. 1987, 52, 4717–4721.
Dho et al., Tetrahedron Lett. 27 (27), 3203–3204, 1986.
Anzeveno et al., J. Org. Chem. 54, 2539–2542 (1989).
Fleet et al., Tetrahedron Lett. 30, 4439–4442 (1989).
Rhinehart et al., J. Pharmacol. Exp. Therap. 241, 915–920 (1987).
Kite et al., Tetrahedron Lett. 29, 6483–6486 (1988).

*Primary Examiner*—Mukund J. Shah
*Assistant Examiner*—Y. N. Gupta
*Attorney, Agent, or Firm*—Scott J. Meyer; James W. Williams, Jr.

[57] ABSTRACT

α-Homojirimycin and 6-dpi-homojirimycin are each synthesized from 2 az ido-2-deoxy-3,4:6,7-di-O-isopropylidene-D-glycero-D-talo-heptono-1,5-lactone in which the side chain acetonide is hydrolyzed to give the corresponding diol which is then protected with a silyl protecting agent to form a silyl ether. The latter compound is used as a divergent intermediate in which the piperidine ring is formed by joining the nitrogen function at C-2 to C-6 (A) with inversion of configuration at C-6 to form 6-epi-homomannojirimycin or (B) with retension of configuration at C-6 to form α-homomannojirimycin.

1 Claim, No Drawings

SYNTHESIS OF MANNOJIRIMYCIN DERIVATIVES

CROSS-REFERENCE TO RELATED APPLICATION

This is a division of application Ser. No. 419,806, filed Oct. 11, 1989, now U.S. Pat. No. 5,011,929 which is a continuation-in-part of application Ser. No. 07/352,068, filed May 15, 1989 now abandoned.

BACKGROUND OF THE INVENTION

This invention relates to a method for the synthesis of mannojirimycin derivatives and, more particularly, to the synthesis of α-homomannojirimycin and 6-epi-homomannojirimycin from the azidolactone, 2-azido-2-deoxy-3,4:6,7-di-O-isopropylidene-D-glycero-D-talo-heptono-1,5-lactone.

Iminoheptitols, such as α-homonojirimycin (1) may constitute a general class of glycosidase inhibitors in which it is possible to use the anomeric substituent to obtain additional potency and/or specificity in comparison to the corresponding azohexoses that lack such a substituent. For example, the β-glucopyranosyl derivative (2) [Anzeveno et al., *J. Org. Chem.*, 54, 2539 (1989); Liu, *J. Org. Chem.*, 52, 4717 (1987)] of α-homonojirimycin (1), the first example of a naturally occurring azoheptose [Kite, et al., *Tetrahedron Lett.*, 29, 6483 (1988)], is a powerful α-glucosidase inhibitor and is a drug candidate for antidiabetic therapy [Rhinehart et al., *J. Pharmacol. Exp. Therap.*, 241, 915 (1987)]. Also, homofuconojirimycin (3) [Fleet et al., *Tetrahedron Lett.*, 30, 4439 (1989)] is as powerful an inhibitor of human liver α-fucosidase as is deoxyfuconojirimycin (4) [Winchester et al., *Biochem. J.*, 259, in press (1989).

Deoxymannojirimycin (DMJ) (5) is a major biochemical tool for the investigation and inhibition of mannosidases of glycoprotein processing [Elbein, *Ann. Rev. Biochem.*, 56, 497 (1987)], although it is a relatively weak inhibitor of α-mannosidases in general. It has been suggested that DMJ may attenuate the infectivity of HIV-1 [Montefiori et al., *Proc. Natl. Acad. Sci. USA* 85, 9248 (1988)] due to its inhibition of processing mannosidases, and molecular graphics studies have been reported in an attempt to design mannosidase inhibitors as potential anti-HIV agents [Winkler and Holan, *J. Med. Chem.* 32, 2084 (1989). In fact, DMJ is a better inhibitor of α-fucosidases than of α-mannosidases [Evans et al. *Phytochemistry,* 24, 1953 (1985)]. This is presumably due to the correspondence of the stereochemistry of the hydroxyl functions at C-2, C-3 and C-4 of DMJ with those in both mannose and fucose and the less stringent structural requirements for the inhibition of α-fucosidase than of α-mannosidase. α-Homomannojirimycin (HMJ) (6) may be a more specific inhibitor of mannosidase than is DMJ (5) because of the additional interaction of the anomeric substituent with the active site of α-mannosidases. Furthermore, HMJ (6) should be a relatively weak inhibitor of α-fucosidases since the configurations at C-2 and C-6 are incorrect in relation to α-fuco configuration; the presence of the polar hydroxymethyl—rather than a methyl—substituent at C-6 should also decrease fucosidase inhibition. Additionally, HMJ should allow the preparation of a number of α-mannosyl derivatives (7) which might allow differential inhibition of the different mannosidases of glycoprotein processing, depending on the nature of the link to the mannose residue.

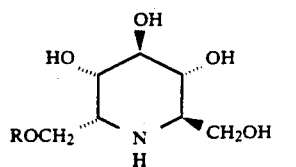

(1) R = H (2) R = β-glucopyranosyl

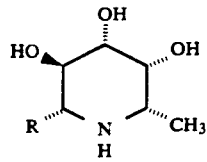

(3) R = CH₂OH (4) R = H

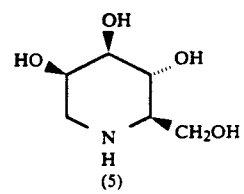

(5)

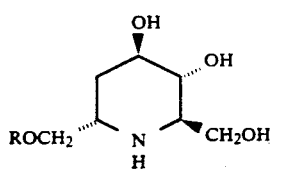

(6) R = H (7) R = linked mannose

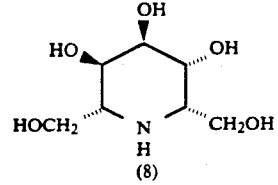

(8)

Homomannojirimycin contains five adjacent chiral centers and seven adjacent carbon atoms, bearing functional groups. Previous syntheses of this class of compounds [Anzeveno et al., supra; Liu, supra; and Fleet et al., *Tetrahedron Lett.* 30, 4439 (1989)], begin with hexose derivatives and add the additional carbon atom relatively late in the synthesis.

BRIEF DESCRIPTION OF THE INVENTION

In accordance with the present invention, α-homomannojirimycin (6) and 6-epi-homomannojirimycin (8) are each synthesized from the protected azidolactone, 2-azido-2-deoxy-3,4:6,7-di-O-isopropylidene-D-glycero-D-talo-heptono-1,5-lactone (10), in which the nitrogen is introduced at C-2. The respective systematic names for α-homomannojirimycin (6) and 6-epi-homomannojirimycin (8) are 2,6-dideoxy-2,6-imino-D-glycero-D-talo-heptitol and 2,6-dideoxy-2,6-imino-L-glycero-D-talo-heptitol.

The azidolactone (10) which is used as a starting material in the method of the invention and its method of synthesis are described in copending application Ser. No. 07/352,068, filed May 15, 1989, and Bruce et al.,

*Tetrahedron* 46, In Press 1989. Briefly, the azidolactone (10) was prepared from diacetone mannose which is converted to the protected heptonolactone (9) by the Kiliani reaction [Kiliani, Ber. 18, 3066 (1885); Fischer, Ber. 22, 2204 (1889)]. Esterification of the protected heptonolactone (9) with triflic anhydride, followed by treatment with sodium azide resulted in overall displacement at C-2 with retention of configuration to give the azidolactone (10) in 76% yield (Example 4 of Ser. No. 07/352,068).

In accordance with the present invention, the side chain acetonide in azidolactone (10) is acid hydrolyzed to give the corresponding diol (11) which is then reacted with a silyl protecting agent, e.g. t-butyldimethylsilyl chloride, to give the silyl ether, 2-azido-7-O-tert-butyldimethylsilyl-2-deoxy-3, 4-isopropylidene-D-glycero-D-talo-heptono-1,5-lactone (12). The silyl ether (12) is then used as a divergent intermediate as follows:

A. to produce 6-epi-homomannojirimycin (8) by a synthetic method which comprises formation of the piperidine ring by joining the nitrogen function at C-2 to C-6 with inversion of configuration at C-6, or B. to produce α-homomannojirimycin (6) by a synthetic method which comprises formation of the piperidine ring by joining the nitrogen function at C-2 to C-6 with retention of configuration at C-6.

In a preferred embodiment of the synthesis of 6-epi-homomannojirimycin (8), the following reaction steps are carried out:

a. Reacting silyl ether (12) with trifluoromethanesulfonic anhydride to give the azidotriflate (13), b. Subjecting the azidotriflate (13) to palladium catalyzed reductive hydrogenation to form the bicyclic lactone (15), c. Reducing the bicyclic lactone (15) with lithium aluminum hydride to give the protected iminoheptitol (16), d. Removing the protecting groups from iminoheptitol (16) by acid hydrolysis, e.g. with trifluoroacetic acid, to give the desired 6-epi-homomannojirimycin (8).

In a preferred embodiment of the synthesis of α-homomannojirimycin (6), the following reaction steps are carried out:

a. Oxidizing the secondary alcohol function in silyl ether (12) to give the corresponding ketoazide (17), b. Reducing the ketoazide (17) with triethylphosphite to give the bicyclic imine (18), c. Reducing the bicyclic imine (18) by lithium borohydride to afford the protected α-homomannojirimycin (19), d. Removing the protecting groups from the protected α-homomannojirimycin (19) by acid hydrolysis, e.g. with trifluoroacetic acid, to give the desired α-homomannojirimycin (6).

Other such suitable reactants for use in the foregoing syntheses of 6-epi-homomannojirimycin and α-homomannojirimycin will be apparent to the person skilled in the art after reading the present disclosure. These reactants are generally used in proportions such as to satisfy the stoichiometry of the above reaction steps.

DETAILED DESCRIPTION OF THE INVENTION

The invention is conveniently illustrated by the following description of preferred embodiments in which the azidolactone, 2-azido-2-deoxy-3,4:6,7-di-O-isopropylidene-D-glycero-D-talo-heptono-1,5-lactone (10), is used to prepare the 6-epi-homomannojirimycin (8) and α-homomannojirimycin (6).

These illustrative embodiments of the invention were carried out by reactions, as follows, in which compound numbers in parenthesis correspond to the compounds shown by structures herein.

A. Synthesis of the divergent intermediate silyl ether (12)

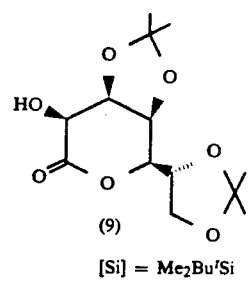

(9)

[Si] = Me$_2$Bu$^t$Si

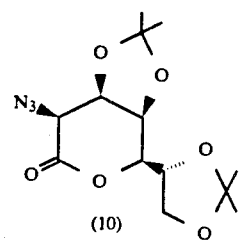

(10)

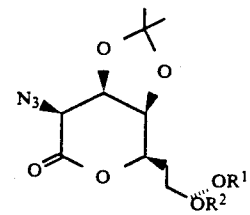

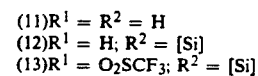

(11) R$^1$ = R$^2$ = H
(12) R$^1$ = H; R$^2$ = [Si]
(13) R$^1$ = O$_2$SCF$_3$; R$^2$ = [Si]

Hydrolysis of the side chain acetonide in (10) by 80% aqueous acetic acid gave the diol (11), m.p. 126°–127° C., (94% yield) which, with tert-butyldimethylsilyl chloride in dimethylformamide in the presence of imidazole, afforded the silyl ether (12), m.p. 138°–139° C., [α]$_D^{20}$+109.6° (c, 0.99 in CHCl$_3$), (79% yield). The silyl ether (12) is a divergent intermediate for both the synthesis of HMJ (6) and of 6-epi-HMJ.

B. Synthesis of 6-epi-homomannojirimycin (8).

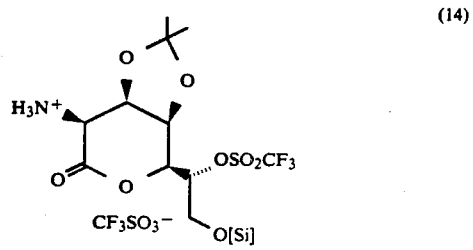

(14)

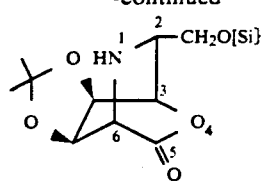

(15)

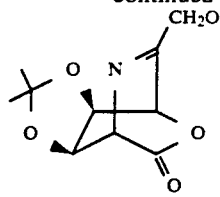

(18)

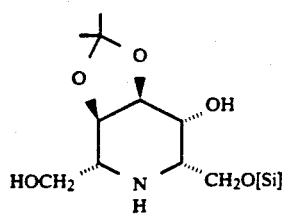

(16)

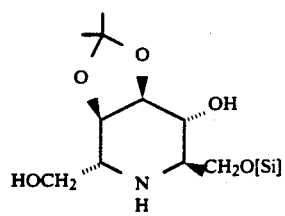

(19)

For the synthesis of 6-epi-HMJ (8), the piperidine ring is constructed by joining the nitrogen function at C-2 in (12) to C-6, with inversion of configuration at C-6. Treatment of (12) with trifluoromethanesulphonic anhydride in the presence of pyridine in dichloromethane at 20° C. gave the triflate (13), m.p. 79°-80° C. (95% yield). Hydrogenation of the azidotriflate (13) in ethyl acetate in the presence of 10% palladium on carbon in the presence of sodium acetate resulted in reduction of azide to the corresponding amine followed by easy cyclization to the bicyclic piperidine (15), waxy solid, $[\alpha]_D^{20} -15.4°$ (c, 1.2 in CHCl$_3$) in 96% yield; when the hydrogenation of (13) was carried out in the absence of sodium acetate, the bicyclic amine (15) was formed in 52% yield, together with the aminotriflate triflate salt (14), m.p. 77°-79° C., $[\alpha]_D^{20} +34.7°$ (C, 0.63 in CHCl$_3$), in 43% yield. Reduction of the bicyclic lactone (15) with lithium aluminum hydride in tetrahydrofuran gave the protected iminoheptitol (16), m.p. 112°-114° C., $[\alpha]_D^{20}$ +52.7° (c, 01.0 in CHCl$_3$), in 54% yield. Removal of the protecting groups from (16) by treatment with aqueous trifluoroacetic acid gave, after purification by ion exchange chromatography, 6-epi-HMJ (8), $[\alpha]_D^{20} +26.4°$ (c, 0.5 in H$_2$O) as a very hygroscopic solid in 85% yield [42% overall yield from (12)]; the corresponding hydrochloride of (8), m.p. 203°-205° C., $[\alpha]_D^{20}+31.1°$ (c, 1.0 in H$_2$O), is an easily crystallized solid. $^{13}$C NMR of 6-epi-HMJ (8) as free base (D$_2$O): δ 54.6 and 56.0 (2×d, C-2 and C-6), 62.1 (two overlapping t, C-1 and C-7), 66.8, 70.1 and 71.7 (3×d, C-3, C-4 and C-5). $^{13}$C NMR of 6-epi-HMJ (8) as hydrochloride (D$_2$O): δ 56.1 and 56.4 (2×d, C-2 and C-6), 58.3 and 59.1 (2×t, C-1 and C-7), 63.5, 67.4 and 69.4 (3×d, C-4 and C-5).

C. Synthesis of α-homomannojirimycin (6)

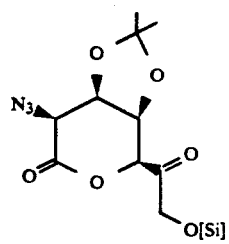

(17)

The synthesis of HMJ (6) from the silyl ether (12) requires the formation of the piperdine ring with retention of configuration at C-6. Oxidation of the secondary alcohol function in (12) with pyridinium chlorochromate in dichloromethane gave the ketone (17), m.p. 120°-122° C., $[\alpha]_D^{20}+5.4°$ (c, 1.0 in CHCl$_3$), in 74% yield. Reduction of the ketoazide (17) with triethylphosphite [Takeuchi et al., *J. Org. Chem.* 54, 431 (1989)] gave an intermediate aza-ylid which underwent an intramolecular aza-Witting reaction [Eguchi and Takeuchi, *J. Chem. Soc. Chem. Commun.* 1989, 602] to give the bicyclic imine (18), oil, $[\alpha]_D^{20}+98.3°$ (c, 1.0 in CHCl$_3$) in 89% yield. Reduction of the imine (18) by lithium borohydride in tetrahydrofuran gave predominant reduction form the less hindered face of the carbon-nitrogen double bond [Maruoka et al., *J. Amer. Chem. Soc.* 105, 2835 (1983)] to afford the protected HMJ (19), m.p. 165°-166° C., $[\alpha]_D^{20}-28.5°$ (c, 1.0 in CHCl$_3$) (46% yield), together with a small amound of the C-6 epimer(16) (2% yield). Removal from (19) of all the protecting groups by aqueous trifluoroacetic acid gave HMJ (6) as a very hygroscopic solid $[\alpha]_D^{20}+7.45°$ (c, 0.55 in H$_2$O), in 92% yield [28% overall yield from (12)]; the hydrochloride of HMJ is also a hygroscopic solid. $^{13}$C NMR of HMJ (6) as free base (D$_2$O): δ 56.2 and 59.0 (2×d, C-2 and C-6), 59.6 and 61.3 (2×t, C-1 and C-7), 68.9, 69.4 and 72.2 (3×d, C-3, C-4 and C-5).

GLYCOSIDASE INHIBITION TESTS

The iminoheptitols (6) and (8) were assayed as inhibitors of 14 human liver glycosidases and the effects compared with those of deoxymannojirimycin (5) by conventional enzyme assay methods described by Daher et al., *Biochem. J.* 258, 613 (1989). The results are set forth in the Table, below, in which it can be seen that the specificity and potency of inhibition of human α-mannosidases by HMJ (6) and by DMJ (5) is very similar. Neither compound inhibited β-mannosidase. 6-epi-HMJ (8) did not inhibit any α-mannosidase, indicating that the correct configuration at C-5 is essential for the inhibition of α-mannosidases. In contrast, both DMJ (5) and 6-epi-HMJ (8) were powerful inhibitors of α-fucosidase, whereas HMJ (6) is only a weak inhibitor of this enzyme. The relative potencies of these compounds as fucosidase inhibitors may be understood by considering them as analogues of α-L-fucose; all three compounds have the correct chirality of the secondary hydroxyl groups—the minimum requirement for inhibition of α-fucosidase. However, their relative effectiveness as α-fucosidase inhibitors is determined by the stereochemistry of the substituents at C-2 and C-6; while DMJ (5) and 6-epi-HMJ (8) have only one substituent with the wrong configuration relative to α-L-fucose, both substituents at C-2 and C-6 of HMJ (6) are different from those in α-L-fucose. All the compounds are weaker inhibitors of α-fucosidase than is deoxyfuconojirimycin, since they all lack a lipophilic methyl substituent with correct configuration.

Thus HMJ (6) is a more selective inhibitor of α-mannosidases than DMJ (5). The enhanced specificity of HMJ (6), relative to DMJ and the possibility of the formations of α-1,2-, α-1,2- and α-1,2-mannosyl derivatives attached to the anomeric hydroxymethyl group should make this a valuable compound for exploring the function and specificity of the processing mannosidases. In summary, the present invention demonstrates the use of the readily available heptonolactone (9) in the synthesis of highly functionalized compounds and further indicates the potential of iminoheptitols as glycosidase inhibitors.

TABLE

% Inhibition of human liver α-fucosidase and α-mannosidase catalysed hydrolysis of 4-umbelliferyl pyrranosides at 1 mM concentration of inhibitor

| Inhibitor | α-Mannosidases | | | α-Fucosidase |
|---|---|---|---|---|
| | Lysosomal | Golgi II | Neutral | |
| Deoxymannojirimycin (5) | 58% | 45% | 21% | 91% [$K_i$ 5.0 μM] |
| Homomannojirimycin (6) | 49% | 56% | 30% | 29% |
| 6-Epi-homomannojirimycin (8) | 0% | 0% | 0% | 96% [$K_i$ 4.5 μM] |

The following examples will further illustrate the invention in greater detail although it will be appreicated that the invention is not limited to these specific examples. Examples 1 to 3 illustrate the preparation of the azidolactone (10); Examples 4 and 5 illustrate the preparation of the divergent intermediate silyl ether (12); Examples 6 to 11 illustrate the preparation of 6-epi-homomannojirimycin (8); and Examples 12 to 15 illustrate the preparation of α-homomannojirimycin (6).

EXAMPLE 1

3,4:6,7-Di-O-isopropylidene-D-glycero-D-talo-heptono-1,5-lactone (9) and 3,4:6,7-Di-O-isopropylidene-D-glycero-D-galacto-heptano-1,5-lactone. D-Mannose was obtained from Sigma Chemical Company and was converted into 2,3:5,6-di-O-isopropylidene-D-mannofuranose in 80%–90% yield as previously described by Schmidt, *Meth. Carbohydr. Chem.* 2, 318 (1963). A mixture 2,3:5,6-di-O-isopropylidene-D-mannofuranose (10.8 g, 41.0 mmol), sodium cyanide (1.84 g, 38.0 mmol) and sodium hydrogen carbonate (3 g) in water (200 ml) was stirred at room temperature for 4 days after which time a clear solution was obtained which was free of cyanide. The reaction mixture was then heated at 90° C. for 1.5 h, cooled to room temperature and extracted with dichloromethane (2×20 ml); the dichloromethane layer was dried (sodium sulphate) and the solvent removed to give unreacted diacetone mannose starting material (1.84 g, 17%). The aqueous layer was adjusted to pH 3 by dropwise addition of concentrated sulphuric acid and then extracted with ethyl acetate (3×150 ml). The combined ethyl acetate extracts were dried (sodium sulphate) and the solvent removed to give a residue which, after purification by flash chromatography [ethyl acetate:hexane, 1:2], gave the following two products:

A 3,4:6,7-di-O-isopropylidene-D-glycero-D-galactoheptono-1,5-lactone, $R_f$ 0.7 (ethyl acetate:hexane, 2:1) and $R_f$ 0.6 (ethyl acetate:hexane, 1:1), (0.78 g, 6.6% yield, 8% based on unrecovered starting material), m.p. 140°–141° C. (ether:hexane), $[\alpha]_D^{20} +93.4°$ (c, 1.2 in CHCl$_3$), $v_{max}$ (CHCl$_3$): 3350 (OH), 1755 (C=O) cm$^{-1}$; (Found: C, 54.17; H, 7.25. C$_{13}$H$_{20}$O$_7$ requires: C, 54.16; H, 7.01%), and

B 3,4:6,7-di-O-isopropylidene-D-glycero-D-talo-heptono-1,5-lactone (9). $R_f$ 0.5 (ethyl acetate:hexane, 2:1) and $R_f$ 0.3 (ethyl acetate:hexane, 1:1), 3.08 g, 26% yield, 31% based on unrecovered starting material), m.p. 157°–159° C. (ethyl acetate:hexane), $[\alpha]_D^{20} +63.8°$ (c, 1.3 in CHCl$_3$), $v_{max}$ (CHCl$_3$): 3540 (OH), 1767 (C=O) cm$^{-1}$; (Found: C, 54.12; H, 7.09. C$_{13}$H$_{20}$O$_7$ requires: C, 54.16; H, 7.01%).

EXAMPLE 2

3,4:6,7-Di-O-isopropylidene-2-O-trifluoromethanesulphonyl-D-glycero-D-talo-heptono-1,5-lactone. Dry pyridine (4 ml, 50 mmol) and trifluoromethanesulphonic anhydride (5.0 g, 18 mmol) were added over 5 min to a stirred solution of the talo-lactone product (9) of Example 1 (3.72 g, 13 mmol) in dichloromethane (75 ml) at −30° C. under nitrogen; after a further 5 min, no starting material remained and the reaction was quenched by addition of dilute aqueous hydrochloric acid (60 ml). The organic layer was washed with brine (2×60 ml) and dried (sodium sulphate); the solvent was removed to give the stable crude triflate (2), a cream solid, (5.1 g, 93%), which was used directly for the conversion to azide without further purification. A sample of the crude triflate was recrystallized to give 3,4:6,7-di-O- isopropylidene-2-O-trifluoromethane sulphonyl-D glycero-D-talo-heptono-1,5-lactone. m.p. 118°–119° C. (dec.) (ether:hexane), $[\alpha]_D^{20} +37.0°$ (c, 1.02 in CHCl$_3$), $v_{max}$ (CHCl$_3$): 1793 (C=O) cm$^{-1}$; Found: C, 40.05; H, 4.59. C$_{14}$H$_{19}$F$_3$O$_9$S requires: C, 40.00; H, 4.56%).

EXAMPLE 3

2-Azido-2-deoxy-3,4:6,7-di-O-isopropylidene-D-glycero-D-talo-heptono-1,5-lactone (10).

From talotriflate. The crude triflate (5.1 g, 12 mmol), prepared above in Example 2, in dimethyl formamide (25 ml) was stirred with sodium azide (1.0 g, 15 mmol) at room temperature for 4 h. The solvent was then removed and the residue partitioned between dichloromethane (60 ml) and brine (60 ml). The organic layer was dried (sodium sulphate) and the solvent removed to give, after purification by flash chromatography [ethyl acetate:hexane, 1:3], 2-azido-2-deoxy-3,4:6,7-di-O-isopropylidene-D-glycero-D-talo-heptono-1,5-lactone (10). [3.05 g, 81%, 75% from the talo-lactone (9)], as a colorless syrup which crystallized on standing, m.p. 103°–104° C. (ether:hexane), $[\alpha]_D^{20} +96.7°$ (c, 1.13 in CHCl$_3$), $v_{max}$ (CHCl$_3$): 2125 (N$_3$), 1773 (C=O) cm$^{-1}$;

(Found: C, 49.81; H, 6.19; N, 13.70. $C_{13}H_{19}N_3O_6$ requires: C, 49.84; H, 6.11; N, 13.41%).

EXAMPLE 4

2-Azido-2-deoxy-3,4-O-isopropylidene-D-glycero-D-talo-heptono-1,5-lactone (11). 2-Azido-2-deoxy-3,4:6,7-di-O-isopropylidene-D-glycero-D-talo-heptono-1,5-lactone (10) (815 mg, 2.6 mmol) was stirred with 80% acetic acid (6 ml) for 3.5 h at 50° C. The solvent was removed and the residue was purified by flash chromatography [ethyl acetate:hexane, 4:1] to give 2-azido-2-deoxy-3,4-O-isopropylidene-D-glycero-D-talo-heptono-1,5-lactone (11), (672 mg, 94%), m.p. 126°-127° C. (ethyl acetate-hexane), $[\alpha]_D^{20} + 131.5°$ (c, 1.08 in MeOH). $\nu_{max}$ (nujol): 3470 (OH), 2120 (Na), 1750 (C=O) cm$^{-1}$ (Found: C, 44.02; H, 5.47; N, 15.22. $C_{10}H_{15}N_3O_6$ requires: C, 43.96; H, 5.53; N, 15.38%).

EXAMPLE 5

2-Azido-7-O-tert-butyldimethylsilyl-2-deoxy-3,4-O-isopropylidene-D-glycero-D-talo-heptono-1,5-lactone (12). A solution of tert-butyldimethylsilyl chloride (0.95 g, 6.3 mmol) in dimethylformamide (5 ml) was added dropwise, under nitrogen, to a stirred solution of the diol (11) (1.15 g, 4.2 mmol) and imidazole (0.57 g, 8.4 mmol) in dimethylformamide (15 ml) at −10° C. After 15 min at −10° C. the reaction was complete and the solvent was removed. Purification by flash chromatography [hexane:ethyl acetate, 4:1] gave 2-azido-7-O-tert-butyldimethylsilyl-2-deoxy-3,4-O-isopropylidene-D-glycero-D-talo-heptono-1,5-lactone (12). (1.29 g, 79%) a white solid, m.p. 138°-139° C. (ether), $[\alpha]_D^{20} + 109.6°$ (c. 0.99 in CHCl$_3$). $\nu_{max}$ (CHCl$_3$) 3550 (OH), 2120 (N$_3$), 1779 (C=O) cm$^{-1}$ (Found: C, 49.34; H, 7.77; N, 10.59. $C_{16}H_{29}N_3O_6Si$ requires: C, 49.59; H, 7.54; N, 10.84%).

EXAMPLE 6

2-Azido-7-O-tert-butyldimethylsilyl-2-deoxy-3,4-O-isopropylidene-6-O-trifluoromethanesulphonyl-D-glycero-D-talo-heptono-1,5-lactone (13). Dry pyridine (0.8 ml, 10 mmol) and trifluoromethanesulphonic anhydride (1.22 g, 4.3 mmol) were added to a stirred solution of 2-azido-2-deoxy-3,4-O-isopropylidene-7-O-tert-butyldimethylsilyl-D-glycero-D-talo-heptono-1,5-lactone (12) (1.29 g, 3.3 mmol) in dichloromethane (15 ml), under nitrogen, at −20° C. After 30 min at −10° C., tlc [ether:hexane, 1:1]indicated complete consumption of starting material (R$_f$ 0.2) to give a single product (R$_f$ 0.6). The reaction was diluted with dichloromethane (20 ml), washed with dilute aqueous hydrochloric acid (2×10 ml), followed by brine (20 ml), and dried (sodium sulphate). The solvent was removed to give the triflate (1.62 g, 95%), a yellow crystalline solid which was used without purification. A small sample was recrystallized to give colorless needles of 2-azido-7-O-tert-butyldimethylsilyl-2-deoxy-3,4-O-isopropylidene-6-O-trifluoromethanesulphonyl-D-glycero-D-talo-heptono-1,5-lactone (13). m.p. 79°-80° C. $[\alpha]_D^{20} + 41.1°$ (c, 0.95 in CHCl$_3$), $\nu_{max}$ (CHCl$_3$): 2125 (N$_3$), 1780 (C=O) cm$^{-1}$ (Found: C, 39.45; H, 5.43; N, 8.26. $C_{17}H_{28}F_3N_3O_8SS_1$ requires: C, 39.30; H, 4.53; N, 8.09%).

EXAMPLE 7

2-Amino-7-O-tert-butyldimethylsilyl-2-deoxy-3,4-O-isopropylidene-6-O-trifluoromethanesulphonyl-D-glycero-D-talo-heptono-1,5-lactone trifluoromethanesulphonate (14). A solution of the triflate (13) (1.62 g, 3.12 mmol) in ethyl acetate (20 ml) was stirred vigorously at room temperature, under hydrogen, in the presence of 10% palladium on carbon (100 mg). After 24 h no starting material remained by tlc (R$_f$ 0.6, ether:hexane, 1:1). The mixture was filtered through celite, washing with ethyl acetate (30 ml), to give a solution containing two products (R$_f$, 0.95 and 0.4, ethyl acetate). The solvent was removed and the residue was purified by flash chromatography (ethyl acetate:hexane, 2:1) to give two compounds; the first was the bicyclic amine (15) (550 mg, 52%), identical in all respects to the material prepared below. The second compound was identified as the triflate salt, 2-Amino-7-O-tertbutyldimethylsilyl-2-deoxy-3,4-O-isopropylidene-6-O-trifluoromethanesulphonyl-D-glycero-D-talo-heptono-1,5-lactone trifluoromethane-sulphonate (14) (872 mg, 43%), a white solid, m.p. 77°-79° C. (ether), $[\alpha]_D^{20} + 34.7°$ (c, 1.0 in CHCl$_3$), $\nu_{max}$ (CHCl$_3$): 3500 br (NH$_3$+), 1780 (C=O) cm$^{-1}$ (Found: C, 33.46; H, 5.04; N, 2.13. $C_{18}H_{31}F_6NO_{11}S_2Si$ requires: C, 33.59; H, 4.85; N, 2.18%).

EXAMPLE 8

7-O-tert-Butyldimethylsilyl-2,6-dideoxy-2,6-imino-3,4-O-isopropylidene-L-glycero-D-talo-heptono-1,5-lactone (15). The azido triflate (13) (605 mg, 1.16 mmol) in ethyl acetate (20 ml) was stirred vigorously at room temperature, under hydrogen, in the presence of anhydrous sodium acetate (380 mg, 4.6 mmol) and 10% palladium on carbon (50 mg). After 20 h. the mixture was filtered through celite, washed with ethyl acetate (20 ml), to give a colorless solution showing one spot on tlc [ethyl acetate, R$_f$ 0.9]. Flash chromatography (hexane:ethyl acetate, 1:1) gave 7-O-tert-butyldimethylsilyl-2,6-dideoxy-2,6-imino-3,4-O-isopropylidene-L-glycero-D-talo-heptono-1,5-lactone (15) (348 mg, 96%, a colorless syrup which solidified to a white wax on standing. $[\alpha]_D^{20} − 15.4°$ (c 1.2 in CHCl$_3$), $\nu_{max}$ (neat): 3360 (NH), 1781 (C=O) cm$^{-1}$; (Found: C, 55.17; H, 8.79; N, 4.27. $C_{16}H_{29}NO_5Si$ requires: C, 55.95; H, 8.51; N, 4.08%).

EXAMPLE 9

Cyclization of the triflate salt (14) to the bicyclic amine (15).

Method (i). The triflate salt (14) (105 mg, 0.16 mmol) was stirred with anhydrous sodium acetate (54 mg, 0.65 mmol) in dimethyl formamide (4 ml) at room temperature for 20 h. The solvent was removed and the residue was purified by flash chromatography (hexane: ethyl acetate, 2.1) to give the bicyclic amine (15) (47 mg, 86%), identical in all respects to the material prepared above.

Method (ii). The triflate salt (14) (75 mg, 0.12 mmol) was stirred with anhydrous sodium carbonate (25 mg, 0.24 mg) in dry tetrahydrofuran (3 ml). After 24 h at room temperature the reaction was worked up and purified as above to give the bicyclic amine (15) (30 mg, 79%).

EXAMPLE 10

7-O-tert-Butyldimethylsilyl-2,6-dideoxy-2,6-imino-3,4-O-isopropylidene-L-glycero-D-talo-heptitol (16).

Method (i). Lithium aluminum hydride (50 mg, 1 mmol) was added to a stirred solution of the bicyclic amine (15) (167 mg, 0.48 mmol) in dry THF (3 ml) at 0° C. After 2 h at 0° C. tlc (hexane:ethyl acetate, 2:1) indicated complete consumption of starting material (R$_f$ 0.6)

to give a product at $R_f$ 0.1 together with baseline material. The reaction was quenched with water (0.5 ml), diluted with ethyl acetate (10 ml) and filtered through celite. The solvent was removed and the residue was purified by flash chromatography (hexane:ethyl acetate, 3:2) to give 7-O-tert-butyl dimethylsilyl-2,6-dideoxy-2,6-imino-3,4-O-isopropylidene-L-glycero-D-talo-heptitol (16) (90 mg, 54%), m.p. 112°–114° C. (ether-hexane), $[\alpha]_D^{20} + 52.7°$ (c, 1.0 in CHCl$_3$, $\nu_{max}$(CHCl$_3$): 3450 (NH cm$^{-1}$ (Found: C, 55.46; H, 9.51; N, 4.03. C$_{16}$H$_{35}$NO$_5$Si requires: C, 55.30; H, 9.57; N, 4.03%).

Method (ii). Lithium borohydride (2 M in THF, 0.55 ml, 1.1 mmol) was added to a stirred solution of the bicyclic amine (15) (379 mg, 1.1 mmol) in THF (10 ml), under nitrogen, at −20° C. The solution was allowed to warm to room temperature and stirred for 2 h, after which time tlc (hexane:ethyl acetate, 1:1) indicated only a trace of starting material ($R_f$ 0.7) and two products at $R_f$ 0.6 and 0.1. The reaction was quenched with anhydrous ammonium chloride, filtered, and the solvent removed to give a solid (383 mg). Flash chromatography (hexane:ether, 2:1) gave two products; the first was the borane adduct (153 mg, 39%), m.p. 110° C. (dec., ether-hexane), $[\alpha]_D^{20} + 9.8°$ (c 1.0 in CHCl$_3$), $\nu_{max}$ (CHCl$_3$): 3450, 3230 (NH and OH), 2380 (BH$_3$) cm$^{-1}$ (Found: C, 53.81; H, 10.34; N, 3.60. BC$_{16}$H$_{32}$NO$_5$Si requires: C, 53.18; H, 10.04; N, 3.88%). The second product was identified as 7-O-tert-butyldimethylsilyl-2,6-dideoxy-2,6-imino-3,4-O-isopropylidene-L-glycero-D-talo-heptitol (16) (74 mg, 18%), identical in all respects to the material prepared above.

EXAMPLE 11

2,6-Dideoxy-2,6-imino-L-glycero-D-talo-heptitol hydrochloride. 7-O-tert-Butyldimethylsilyl-2,6-dideoxy-2,6-imino-3,4-O-isopropylidene-L-glycero-D-talo-heptitol (16) (137 mg, 0.40 mmol) was stirred in 50% aqueous trifluoroacetic acid (4 ml) for 20 h at room temperature. The solvent was removed and the crude trifluoroacetate salt was decomposed with dilute aqueous sodium hydroxide. Purification by ion exchange chromagoraphy (Dowex 50 x, 8–100, H+ form, eluting with 0.5 M aqueous ammonia), followed by freeze drying, gave 2,6-dideoxy-2,6-imino-L-glycero-D-talo-heptitol (8), (66 mg, 85%), a very hygroscopic solid, ($R_f$ 0.8, EtOH : MeOH : 0.5 M NH$_3$ 2:2:1), $[\alpha]_D^{20} + 26.4°$ (c, 0.5 in H$_2$O). Repeating this procedure with the borane adduct (8) (125 mg, 0.35 mmol) gave an identical material to that above (55 mg, 82%). The free base (16) (100 mg, 0.52 mmol) was dissolved in methanol (3 ml) and acetyl chloride (ca. 0.1 ml, 1 mmol) was added. Addition of chloroform and cooling yielded crystals of 2,6-dideoxy-2,6-imino-L-glycero-D-talo-heptitol hydrochloride, (91 mg, 76%). m.p. 203°–205° C. (methanol:chloroform), $[\alpha]_D^{20} + 31.1°$ (c, 1.0 in H$_2$O), $\nu_{max}$ (KBr): 3500–2500 (NH, OH) cm$^{-1}$ Found: C, 36.61: H, 7.32; N, 5.88. C$_7$H$_{16}$NO$_5$Cl requires: C, 36.61; H, 7.02; N, 6.10%.

EXAMPLE 12

2-Azido-7-O-tert-butyldimethylsilyl-2-deoxy-3,4-O-isopropylidene-D-talo-6-heptulosono-1,5-lactone (17). The alcohol (12) (2.07 g, 5.35 mmol) and pyridinium chlorochromate (3.45 g, 16 mmol) were stirred with powdered molecular sieve (2 g) in dichloromethane (50 ml), under nitrogen, at room temperature. After 18 h, tlc (hexane:ethyl acetate, 1:1) indicated complete consumption of starting material ($R_f$ 0.35) to give a single product ($R_f$ 0.5). The mixture was diluted with ether (50 ml), filtered through a celite plug and the solvent removed. Flash chromatography (hexane:ethyl acetate, 5:1) gave 2-Azido-7-O-tert-butyldimethylsilyl-2-deoxy-3,4-O-isopropylidene-D-talo-6-heptulosono-1,5-lactone (17), (1.53 g, 74%), m.p. 120°–122° (ether), $[\alpha]_D^{20} + 5.4°$ (c, 1.0 in CHCl$_3$), $\nu_{max}$ (CHCl$_3$): 2123 (N$_3$), 1780 (C=O), 1743 (C=O) cm$^{-1}$ (Found: C, 49.96; H, 7.32; N, 10.60. C$_{16}$H$_{27}$N$_3$O$_6$Si requires: C, 49.85; H, 7.06; N, 10.90%).

EXAMPLE 13

Imine (18)

Triethyl phosphite (1.3 M in THF, 2.4 ml, 3.1 mmol) was added, under nitrogen, to a stirred solution of the ketone (17) (605 mg, 1.57 mmol) in dry THF (5 ml). After 18 h at room temperature, tlc (hexane:ethyl acetate, 5:1) indicated complete consumption of starting material ($R_f$ 0.6) to give a single product ($R_f$ 0.7). The solvent was removed and the residue was purified by flash chromatography (hexane:ethyl acetate, 5:1) to give the bicyclic imine (18), (477 mg, 89%), a colorless oil, $[\alpha]_D^{20} + 98.3°$ (c, 1.0 in CHCl$_3$), $\nu_{max}$ (film) 1780 (C=O), 1650 (C=N) cm$^{-1}$ (Found: C, 56.39; H, 8.02; N, 4.05. C$_{16}$H$_{27}$NO$_5$Si requires: C, 56.28; H, 7.97; N, 4.1%).

EXAMPLE 14

7-O-tert-Butyldimethylsilyl-2,6-dideoxy-2,6-imino-3,4-O-isopropylidene-D-glycero-D-talo-heptitol (19). Lithium borohydride (2 M in THF, 0.6 ml, 1.2 mmol) was added, under nitrogen, to a stirred solution of the imine (18) (182 mg, 0.53 mmol) in dry THF (10 ml) at −78° C. The solution was allowed to warm to room temperature over a period of 1 h and stirred for an additional 4 h before quenching with saturated aqueous ammonium chloride (0.3 ml). The solution was evaporated to dryness and the residue was purified by flash chromatography (gradient elution; hexane:ethyl acetate, 1:1 0:1) to give two products; the first ($R_f$ 0.3, ethyl acetate) was 7-O-tert-butyldimethylsilyl-2,6-dideoxy-2,6-imino-3,4-O-isopropylidene-D-glycero-L-talo-heptitol (16) (3 mg 2%), identical in all respects to the material prepared above. The second compound was identified as 7-O-tert-butyldi-methylsilyl-2,6-dideoxy-2,6-imino-3,4-O-isopropylidene-D-glycero-D-talo-heptitol (19), (85 mg, 46%), m.p. 165°–166° C. (ethyl acetate:ether), $[\alpha]_D^{20} − 28.5°$ (c, 1.0 in CHCl$_3$), $\nu_{max}$ (CHCl$_3$) 3450 (OH) cm$^{-1}$. Found C, 55.56; H, 10.01; N, 3.99. C$_{16}$H$_{35}$NO$_5$Si requires: C, 55.30; H, 9.57; N, 4.03%).

EXAMPLE 15

2,6-Dideoxy-2,6-imino-D-glycero-D-talo-heptitol (6). The protected iminoheptitol (19) (196 mg, 0.56 mmol) in 50% aqueous trifluoroacetic acid (4 ml) was stirred at room temperature for 20 h. After removing the solvent, the resulting trifluoroacetate salt was decomposed to the free base with dilute aqueous sodium hydroxide. Purification by ion exchange chromatography (Dowex 50 x, 8–100, H+ form, eluting with 0.5 M aqueous ammonia solution and then Amberlite CG-400, OH− form, eluting with water) gave, after freeze drying, 2,6-dideoxy-2,6-imino-D-glycero-D-talo-heptitol (6) (99 mg, 92%), a very hygroscopic solid, $[\alpha]_D^{20} + 7.45°$ (c, 0.55 in H$_2$O).

Various other examples will be apparent to the person skilled in the art after reading the present disclosure without departing from the spirit and scope of the invention. It is intended that all such other examples be included within the scope of the appended claims.

What is claimed is:

1. 7-O-tert-Butyldimethylsilyl-2,6-dideoxy-2,6-imino-3,4-O-isopropylidene-L-glycero-D-talo-heptono-1,5-lactone.

* * * * *